United States Patent
Fürtinger et al.

(10) Patent No.: US 9,119,789 B2
(45) Date of Patent: Sep. 1, 2015

(54) STABLE AQUEOUS G-CSF FORMULATIONS

(75) Inventors: Sabine Fürtinger, Innsbruck (AT); Heinrich Matous, Wörgl (AT)

(73) Assignee: SANDOZ AG, Basel (CH)

( * ) Notice: Subject to any disclaimer, the term of this patent is extended or adjusted under 35 U.S.C. 154(b) by 907 days.

(21) Appl. No.: 12/530,671

(22) PCT Filed: Apr. 4, 2008

(86) PCT No.: PCT/EP2008/002700
§ 371 (c)(1),
(2), (4) Date: Dec. 22, 2009

(87) PCT Pub. No.: WO2008/122415
PCT Pub. Date: Oct. 16, 2008

(65) Prior Publication Data
US 2010/0104627 A1    Apr. 29, 2010

(30) Foreign Application Priority Data
Apr. 5, 2007 (EP) .................... 07007221

(51) Int. Cl.
  *A61K 38/24* (2006.01)
  *C07K 1/00* (2006.01)
  *A61K 9/19* (2006.01)
  *A61K 38/19* (2006.01)
  *A61K 47/18* (2006.01)

(52) U.S. Cl.
  CPC ............... *A61K 9/19* (2013.01); *A61K 38/193* (2013.01); *A61K 47/183* (2013.01)

(58) Field of Classification Search
None
See application file for complete search history.

(56) References Cited

U.S. PATENT DOCUMENTS

| 5,919,443 | A | 7/1999 | Michaelis et al. |
| 6,908,610 | B1 * | 6/2005 | Sato ............................ 424/85.1 |
| 7,585,496 | B2 * | 9/2009 | Podobnik et al. ............ 424/85.1 |
| 2008/0026046 | A1 * | 1/2008 | Skufca et al. ................. 424/450 |
| 2010/0028372 | A1 | 2/2010 | Jezek |

FOREIGN PATENT DOCUMENTS

| EP | 1 329 224 A1 | 7/2003 |
| EP | 1 197 221 B1 | 5/2006 |
| JP | 2007-204498 | 8/2007 |
| WO | WO2005/042024 | 5/2005 |

OTHER PUBLICATIONS

Characteristics of Mutated G-CSF Formulation "Neu-up" (Nartograstim), Antibiotics & Chemotherapy 11[2] (1995) pp. 100-105; Masumitsu Takasugi.
Granulocyte-colony stimulating factor maintains a thermally stable, compact, partially folded structure at pH 2, Carl G. Kolvenbach, et al., The Journal of Peptide Research, vol. 50, pp. 310-318.

* cited by examiner

*Primary Examiner* — Shulamith H Shafer
(74) *Attorney, Agent, or Firm* — O'Melveny & Myers LLP

(57) ABSTRACT

The invention relates to stable glutamate-buffered G-CSF formulations having a pH of from 3.5 to 4.8. The invention further concerns lyophilisates and powders obtainable from such formulations, and to pharmaceutical kits containing such lyophilisates and powders.

18 Claims, 2 Drawing Sheets

STABLE AQUEOUS G-CSF FORMULATIONS

Figure 1:
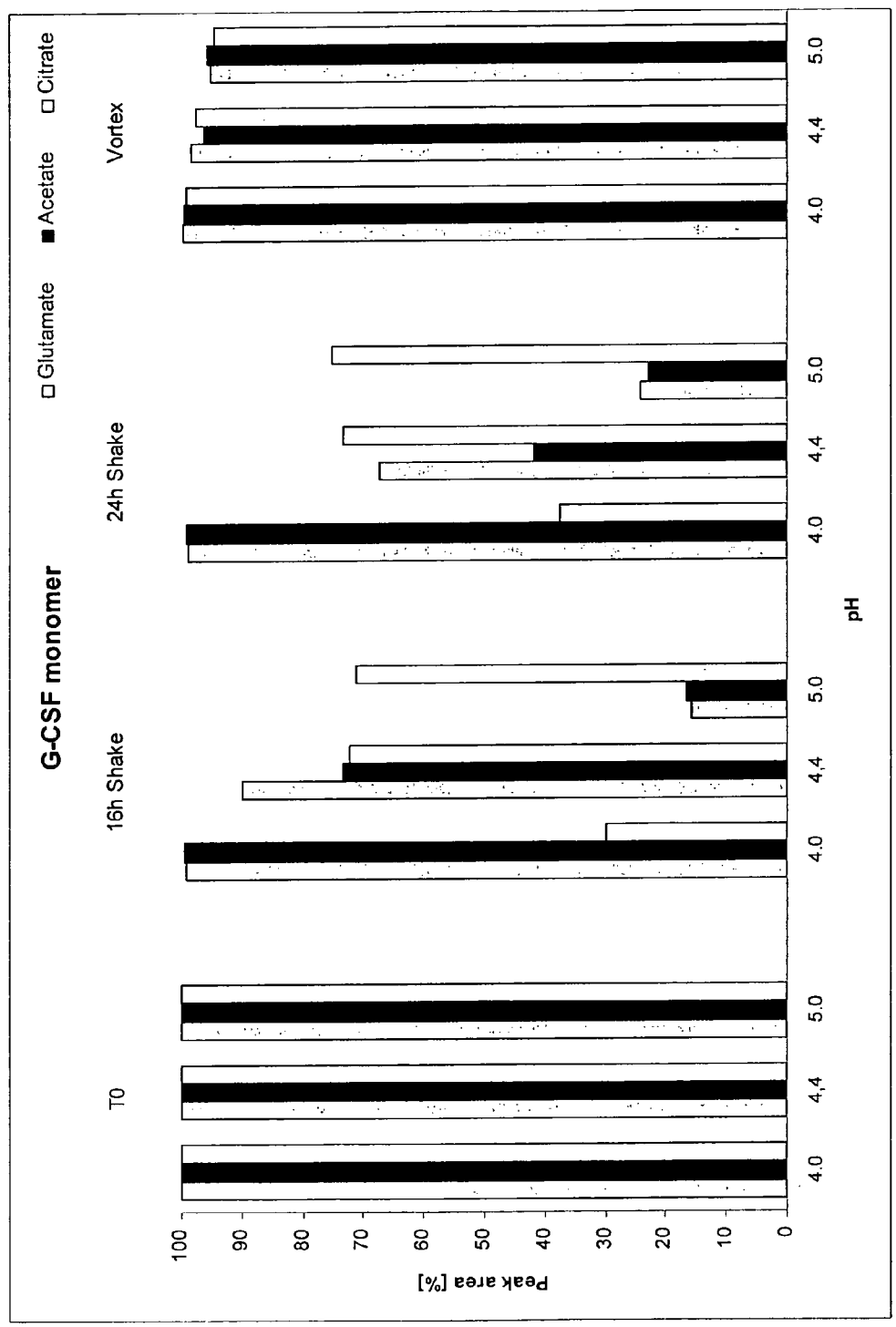

The present invention relates to stable aqueous G-CSF formulations, to G-CSF-lyophilisates or G-CSF-powders, as well as to pharmaceutical kits containing these lyophilisates or powders.

G-CSF (Granulocyte-Colony Stimulating Factor) is a naturally occurring growth factor which belongs to the family of cytokines. G-CSF plays a crucial role in hematopoiesis and enhances maturation, proliferation, differentiation and survival of neutrophils and neutrophilic successor cells. Clinically, G-CSF is mainly used for controlling tumors and, in particular, for the treatment of neutropenia following chemotherapy, and it is also applied for bone marrow transplantations and in the treatment of infectious diseases.

Human G-CSF in its naturally occurring form is an about 20 kDa glycoprotein which has five cysteine residues. Four of these residues form two intramolecular disulfide bridges which are crucial for the activity of the protein. As G-CSF is obtained only in small amounts from natural sources, mainly recombinant forms of G-CSF are used for preparing medicaments. Recombinant G-CSF may be obtained, for instance, by expressing the protein in mammalian cells, such as CHO (Chinese Hamster Ovary) cells, or in procaryotic cells, such as *E. coli*. Recombinant proteins expressed in mammalian cells have a glycosylation pattern different from that of naturally occurring G-CSF. Proteins expressed in *E. coli* are not glycosylated, these proteins, however, may have an additional N-terminal methionine residue.

Due to the high hydrophobicity of the protein, formulations of G-CSF are relatively unstable, in particular in case of the non-glycosylated recombinant forms of the protein. The molecule easily adsorbs to the walls of vials, syringes or the like and forms dimers and higher aggregates. Moreover, it is subject to chemical modifications such as deamidation, oxidation, cleavage of disulfide bridges or proteolysis. This often results in loss of activity, particularly upon prolonged storage of the protein. This is not only costly but also is undesirable for therapeutic reasons, for example if the G-CSF is to be administered over a prolonged period of time at a constant dosage. Furthermore the products formed, for example, by dimerization, oxidation or degradation, may cause undesired immune responses. Conventional G-CSF formulations, in addition, are sensitive to mechanical stress as may occur, e.g., as a result of shaking of the liquid formulations during transport, and to single or repeated freezing and thawing. This may also result in the formation of higher aggregates and loss of activity.

DE-A-37 23 781 describes medicaments containing G-CSF as the active ingredient, which contain at least one pharmaceutically acceptable surfactant, saccharide, protein, or high-molecular weight compound for stabilizing the active ingredient. Surfactants such as polyoxyethylene sorbitan esters of aliphatic fatty acids are used in combination with human serum albumine and mannitol. The surfactants are preferably used in an amount of from 1 to 10,000 parts by weight per part by weight of G-CSF. The aqueous phosphate-buffered formulations, for which a pH value of 7.4 is specified, are stable at 4° C. over a prolonged period of time. Due to their antigenic properties, however, proteins and peptides of human and animal origin, may cause undesired immunological reactions.

EP-A-0 373 679 discloses that G-CSF of G-CSF having a pH value of from 2.75 to 4.0 and low conductivity, which may be stored over prolonged periods of time. Preferably, no buffer is used in these formulations in order to avoid the aggregation of G-CSF. If any, carboxylic acids, citric acid, lactic acid or tartaric acid may be used in small amounts of less than 2 mM as buffer substances. These conditions, however, do not allow long-term stabilization of formulations having a pH value above 4.0.

Herman, A. G. et al. ("Characterisation, Formulation, and Stability of Neupogen® (Filgrastim), a Recombinant Human Granulocyte-Colony Stimulating Factor." In: Formulation Characterisation and Stability of Protein Drugs, pp. 303-328, R. Pearlman and Y. J. Wang, Eds., Plenum Press, New York, 1996) describe stabilized compositions of non-glycosylated recombinant G-CSF which contain 10 mM of sodium acetate, pH 4.0, 5% of mannitol and 0.004% of Polysorbate 80. Such compositions are stable for more than 24 months at 2-8° C.

WO-A-94/14466 discloses aqueous pharmaceutical G-CSF-preparations containing acetic acid, lactic acid, citric acid, maleic acid, phosphoric acid, arginine and salts thereof as buffers. These preparations have a pH value in the range of from 2.5 and 5.0 and of from 7 to 8. In these formulations, the formation of multimers and aggregates of G-CSF due to mechanical stress, as may occur, e.g., during shaking of the solutions, is reduced.

EP-A-0 306 824 describes stabilized phosphate-buffered preparations of human proteins, in particular erythropoietin, wherein stabilization is achieved by adding urea, amino acids and detergent.

EP-A-1 060 746 discloses phosphate-buffered G-CSF-containing formulations having a pH of from 5 to 7, which contain a surfactant in an amount of 1 part by weight or less per part by weight of G-CSF.

WO-A-94/14465 discloses lyophilized pharmaceutical G-CSF-preparations and aqueous preparations obtainable therefrom. These formulations contain maltose, saccharose, raffinose, trehalose or amino sugars as stabilizing agents. pH-stabilization is preferably achieved by arginine buffers. Further addition of antioxidants, reducing agents and amino acids such as glutamic acid had no significant influence on the stability of the lyophilisates.

EP-A-1 197 221 discloses long-term stable G-CSF formulations at a pH of from 5 to 7, which contain one or more amino acids of the group of lysine, histidine, arginine, aspartic acid, glutamic acid, threonine and asparagine, as well as one or more hydrophobic amino acids. In order to avoid oxidation of methionine residues in the G-CSF molecule, the amino acid methionine is added to the formulation.

US-A-2007/0053871 discloses aqueous G-CSF-containing formulations, which comprise an antimicrobial agent and an osmolyte, such as glycerol, sorbitol, sarcosine or sucrose, to mitigate the destabilizing effect of the antimicrobial agent. Examples for buffers are acetate, succinate, gluconate, citrate and histidine.

WO-A-2005/039620 discloses succinate- and tartrate-buffered compositions stable over a wide pH range.

WO-A-2006/138181 discloses compositions containing a pharmaceutical protein, wherein the composition is buffered by the protein itself. One protein among a large number of pharmaceutical proteins mentioned is filgrastim.

The object of the present invention was to provide an aqueous G-CSF formulation suitable for pharmaceutical use, which is stable over prolonged periods of time without the need of large amounts of various types of stabilizers even under conditions of mechanical stress and at elevated temperatures.

This object has been achieved by a liquid aqueous glutamate-buffered G-CSF formulation having a pH of from 3.5 to 4.8.

The invention further concerns lyophilisates and powders obtainable from said formulation.

It has surprisingly been found that glutamate-buffered aqueous G-CSF formulations having a pH value of from 3.5 to 4.8 are long-term stable at elevated temperatures, even if the formulation is essentially free from sugars, aminosugars and amino acids other than glutamic acid/glutamate, such as arginine. Formation of aggregates (dimers and higher multimers of G-CSF) only occurs at low levels, and activity is maintained even at prolonged storage. Even under conditions of mechanical stress, as might occur, for example, when reconstituting G-CSF-containing lyophilisates or powders, filtering of G-CSF formulations, filling into vials, charging syringes, during transport and upon repeated freezing and thawing, undesirable formation of aggregates or other secondary reactions of the G-CSF protein are sufficiently prevented.

The invention further concerns a method for preparing the formulation of the present invention, wherein said method comprises combining G-CSF with a glutamate-buffered aqueous solution having a pH value of from 3.5. to 4.8.

The invention further concerns a pharmaceutical kit for preparing the formulations of the invention, wherein said kit comprises, physically separated:
a) a G-CSF-containing lyophilisate or powder; and
b) a glutamate-buffered aqueous solution having a pH value of from 3.5 to 4.8 for reconstituting the G-CSF-containing lyophilisate or powder.

Figure 2:
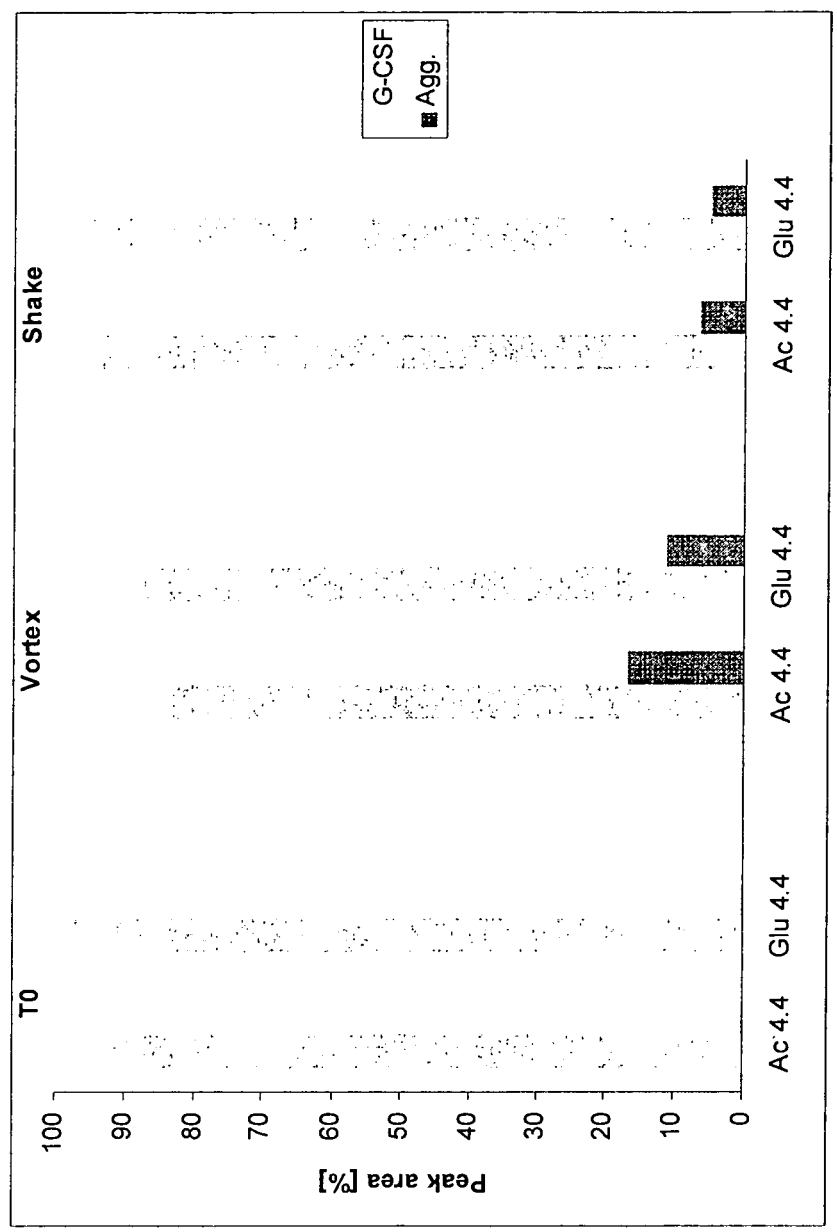

Further embodiments of the invention are apparent from the claims and from the following description and drawings, where FIG. 1 shows the content of monomeric G-CSF, determined by SEC (expressed as % peak area), in glutamate-, acetate- and citrate-buffered G-CSF formulations at different pH values after shaking for 16 h at 180 apm and 24 h at 230 apm, and vortexing for 120 sec; and FIG. 2 shows the content of monomeric G-CSF and of aggregates of G-CSF, determined by SEC (expressed as % peak area), in acetate- and glutamate-buffered G-CSF formulations having a pH of 4.4, which are free from tonicity agents and surfactants, after vortexing for 120 sec and shaking for 16 h at 180 apm.

The G-CSF protein in the formulations of the present invention may be any mammalian G-CSF, in particular human G-CSF, or variants or fragments derived therefrom, as far as they have substantially the same biological activity in hematopoiesis as mammalian, in particular human G-CSF protein. As used herein, the term G-CSF includes both G-CSF derived from natural sources as well as synthetic or recombinant G-CSF as well as variants and fragments thereof, e.g., recombinant human proteins having an N-terminal methionine residue obtained when expressing the G-CSF gene in procaryotes, fusion proteins of G-CSF, as well as G-CSF proteins obtained by substitution, deletion or insertion of one or more amino acids of the naturally occurring G-CSF. The G-CSF may be glycosylated or non-glycosylated. Non-glycosylated G-CSF is obtained, e.g., by expression in procaryotic cells such as *E. coli*, whereas glycosylated G-CSF may be obtained either by isolation from natural sources, by expression in eucaryotic cells such as CHO cells, or by artificial glycosylation. Artificially modified G-CSF may be obtained, e.g., by enzymatic glycosylation or by chemical PEGylation. G-CSF variants useful in the formulations of the present invention are disclosed, e.g., in EP-A-0 456 200. Preferably, recombinant non-glycosylated G-CSF is used in the formulations of the invention; in a more preferred embodiment, the G-CSF comprises the amino acid sequence of human G-CSF as indicated, e.g., in DE-A-37 23 781, or a sequence derived therefrom.

The buffer system of the formulations of the present invention essentially consists of a glutamic acid/glutamate system, i.e., the formulation of the invention is essentially free from other buffering agents. The glutamic acid/glutamate system used according to the invention can be prepared, for example, starting from glutamic acid and/or a salt thereof and adjusting the pH to the desired value using a suitable inorganic acid or base such as hydrochloric acid or an alkaline or alkaline earth hydroxide. Physiologically acceptable glutamic acid salts are preferred, e.g., alkali, alkaline earth, or ammonium salts. Alkali or ammonium salts are preferred, in particular the monosodium salt. Preferably, the buffer is prepared starting from glutamic acid and the pH value adjusted using a suitable inorganic base, for example sodium hydroxide.

The pH value of the formulation of the invention is of from 3.5 to 4.8, preferably of from 3.7 to 4.7. More preferably the pH is of from 3.9 to 4.6, for example of from 4.2 to 4.6, more specifically of from 4.3 to 4.5.

The concentration of the glutamate buffer is advantageously adjusted so as to achieve a pH-stabilizing effect at the desired pH value and a sufficient buffer capacity. Usually, the glutamate buffer has a concentration of at least 0.5 mM, preferably of from 1 to 100 mM, and more preferably of from 2 to 80 mM. Buffer concentrations of from 2 to 40 mM, in particular of from 2 to 25 mM, for example of from 5 to 15 mM, will provide sufficient stability and will be sufficiently low to avoid an undesired reaction in the tissue at the injection site. However, a buffer concentration of 40 mM and more, for example of from 40 to 60 mM, may further increase stability under certain conditions of stress.

The concentration of G-CSF in the formulation of the present invention will depend on the intended use. The upper concentration limit results from the solubility of G-CSF in the buffer. In pharmaceutical formulations, G-CSF is present in a pharmaceutically effective amount, and the concentration usually is not more than 5 mg/ml. Usually, the concentration is of from 0.0001 to 5 mg/ml, preferably of from 0.0005 to 4 mg/ml, more preferably of from 0.001 to 2.5 mg/ml, and most preferably of from 0.01 to 2.0 mg/ml, for example of from 0.1 to 1.5 mg/ml. In bulk solutions (starting solutions having higher concentrations), however, the concentration may even be 10 mg/ml and more.

In a preferred embodiment of the invention, the formulation contains one or more surfactants, in particular one or more non-ionic surfactants. Preferably, the non-ionic surfactant is selected from the group consisting of fatty alcohol ethoxylates, alkylpolyglycosides, polyoxyalkylenes, polysorbates or mixtures of two or more thereof. Polyoxyalkylenes such as polyoxyalkylene block copolymers, for example Poloxamer 188 (available under the trade name Pluronic F68), and polysorbates, i.e., polyoxyethylene sorbitan esters of aliphatic fatty acids are preferred. Most preferred are polysorbates such as polyoxyethylene sorbitan monolaurate (available under the trade name Tween 20), polyoxyethylene sorbitan monopalmitate (Tween 40), polyoxyethylene sorbitan monostearate (Tween 60), polyoxyethylene sorbitan tristearate (Tween 65), polyoxyethylene-sorbitan monooleate (Tween 80) and polyoxyethylene sorbitan trioleate (Tween 85). Polyoxyethylene sorbitan monopalmitate and polyoxyethylene sorbitan monooleate are most preferred. Surfactants are preferably added in the formulation in an amount of lower than 5 mg/ml, for example in an amount of 1 mg/ml or lower. Preferably, surfactants, in particular polysorbates, are used in amounts of from 0.001 to 0.4 mg/ml, more preferably of from 0.005 to 0.3 mg/ml, and most preferably of from 0.01 to 0.2 mg/ml.

Advantageously, the formulations of the invention are isotonic with the patient's blood, in particular when used for pharmaceutical purposes such as injection or infusion. While suitably adjusting the concentrations of the glutamate buffer may provide the desired tonicity, the addition of further tonicity agents, in particular sugar alcohols, will be preferred. Suitable sugar alcohols are, for example, mannitol and sorbitol, with sorbitol being particularly preferred. Tonicity agents are usually added in amounts of up to 200 mg/ml of the formulation. Preferably, amounts of up to 100 mg/ml, more preferably of from 5 to 80 mg/ml, for example of from 10 to 70 mg/ml, and most preferably of from 20 to 60 mg/ml, are used. Preferably, the formulations of the invention are essentially free from sugars and aminosugars. The term "essentially free", as used herein with reference to a certain molecule means that the amount of said molecule, if present at all, does not exceed trace amounts and preferably is less than 0.01 µg/ml formulation.

Preferably, the formulation of the invention is essentially free from free amino acids or amino acid salts other than glutamic acid/glutamate. In particular, the formulation of the invention is essentially free from arginine and/or salts thereof.

If desired, the formulation of the invention may contain one or more reducing agents, in particular sulfur-containing reducing agents. Suitable reducing agents are, for example, thioglycerol, glutathione, dithioglycol, thiodiglycol, N-acetylcysteine, thiosorbitol, thioethanolamine, sodium thiosulfate, sodium hydrogensulfite, sodium pyrosulfite and dithiothreitol. Reducing agents are suitably used in concentrations of from 0.1 to 100 mM, preferably of from 1 to 50 mM. The use of reducing agents, however, is not necessary and, therefore, the formulation of the invention preferably free from reducing agents.

If desired, the formulation of the invention may contain one or more antioxidants Suitable antioxidants are, for example, ascorbic acid or a salt thereof, ascorbic acid palmitate, ascorbic acid stearate, triamyl gallate, α-tocopherol, tocopherol acetate and butylhydroxyanisol. Antioxidants are suitably used in concentrations of from 0.1 to 100 mM, preferably of from 1 to 50 mM. The use of antioxidants, however, is not necessary and, therefore, the formulation of the invention preferably is free from antioxidants.

If desired, the formulation of the invention may also contain one or more chaotropic agents. Suitable chaotropic agents are, for example, urea, guanidinium hydrochloride or guanidinium isocyanate. Chaotropic agents are suitably used in concentrations of from 0.1 to 50 mM, preferably of from 1 to 30 mM. Use of chaotropic agents, however, is not required in the formulations of the invention and, therefore, the formulation of the invention preferably is free from chaotropic agents.

Although the formulation of the invention may contain complexing agents such as carboxylic acids, for example citrate, the addition of such substances is not preferred and the formulation preferably is essentially free from carboxylic acids or carboxylic acid salts other than glutamic acid/glutamate.

If desired, the G-CSF formulations of the invention may also contain additional proteins and protein-like molecules such as human serum protein. Due to the risks involved with foreign proteins, however, the formulation is essentially free from proteins as a stabilizer.

In a preferred embodiment of the invention, the aqueous formulation of the invention consists of an aqueous glutamate-buffer, preferably a Na-glutamate buffer, which contains, as the sole components, a G-CSF molecule as the active ingredient, a surfactant, preferably polyoxyethylene-sorbitan monooleate (Tween 80), and a tonicity agent, preferably a sugar alcohol, for example sorbitol.

The G-CSF formulations according to the invention have a high shelf live or storage stability, i.e., there is only a minor loss of G-CSF protein after long term storage due to adsorption, degradation or aggregation of the protein. Preferably, the content of G-CSF protein (hereinafter also referred to as "G-CSF content") in the formulations of the present invention after long term storage at 5° C. for 24 months is at least 95% of the initial G-CSF content in the formulations, as determined, for example, by RP-HPLC as described below. The G-CSF content of the formulations of the present invention after long term storage at 25° C. for 6 months typically is at least 90% of the initial G-CSF content of the formulations, as determined, for example by RP-HPLC.

The formulations of the invention may be prepared in a manner known per se. Usually, the buffer substances, for example glutamic acid or a salt thereof, and, optionally, other additives like surfactants and tonicity agents are dissolved in a suitable amount of an aqueous solvent, usually water. If necessary, the pH value is adjusted using a suitable acid or base as those mentioned above. Following a sterilization step, such as filtration through a sterile filter, G-CSF is added in the desired concentrations. It is also possible, however, to first provide G-CSF in an aqueous solution and then to adjust the pH to the desired value using a glutamate buffer system.

The formulations of the present invention are particularly useful as pharmaceutical preparations, where all optional ingredients have to be physiologically acceptable. These pharmaceutical preparations may be used in various application forms, but preferably are preparations for injection or infusion, in particular for intravenous, intramuscular, or subcutaneous administration. The formulations of the invention may, however, also be used for the preparation of application forms such as hydrogels or liposomes. The pharmaceutical preparations of the invention may be used for any indication for which G-CSF may be employed, such as for the treatment of neutropenia, for bone marrow transplantations, and in the treatment of infectious diseases and of tumor diseases.

G-CSF-containing lyophilisates and powders may be obtained from the aqueous formulations of the invention in a manner known per se, for example by lyophilization or spray-drying. Upon reconstitution of such lyophilisates and powders, G-CSF formulations are obtained which are stable over a prolonged period of time even at elevated temperatures.

For easy preparation of the aqueous formulations of the invention, the components of the formulations may be provided in the form of a pharmaceutical kit. Such a kit will comprise, physically separated: a) a G-CSF-containing lyophilisate or powder; and b) an aqueous glutamate-buffered solution having a pH value of from 3.5 to 4.8 for reconstituting the G-CSF-containing lyophilisate or powder. Optional ingredients such as surfactants and tonicity agents, as may be desired for the formulations of the invention, may be contained in the lyophilisate/powder portion and/or in the aqueous solution. In this way, formulations according to the invention may be prepared at any desired time, e.g., by the medical personnel.

The present invention will now be illustrated in more detail with reference to the following examples and figures which are not intended to be limiting the invention.

EXAMPLES

Material and Methods

1. Preparation of Buffered G-CSF Formulations

Aqueous G-CSF-solutions at a concentration of up to 2 mg/ml were diluted at ambient temperature with the respective buffer solutions to a G-CSF-content of 0.6 or 0.96 mg/ml. Buffer solutions were prepared by first adding the respective acid (glutamic acid, acetic acid, succinic acid) or basic salt (sodium citrate, Tris) components in the desired molar concentrations and adjusting the pH to the desired value using sodium hydroxide solution or hydrochloric acid solution, respectively. If required, buffer solutions also contained surfactants and tonicity agents in the desired amounts. The compounded solutions were subjected to filtration through a sterile filter (pore size 0.2 μm, Millipore®) and aliquots were filled into 4 ml 2R glass vials or 1 ml syringes made of glass of hydrolytic class I and closed with a rubber stopper.

2. Conditions of Mechanical Stress 2.1 Shaking Stress

Shaking stress was generated by horizontal movement on a shaking plate creating motion and renewal in the air-water interface. 2R vials each containing 1 ml of G-CSF formulation were horizontally placed on a shaker platform and agitated at 180 or 230 apm (amplitudes per minute) at controlled ambient temperature. After 16 h and 24 h, three vials per time point were removed and analyzed for protein aggregates (dimers and higher multimeric G-CSF molecules). Three unstressed vials, exposed to light, and vials stored at 2-8° C. were analyzed as control. Furthermore, vials containing the respective solutions without G-CSF were included in all stress experiments to exclude a matrix effect.

2.2 Vortexing Stress

Vortexing was performed using 2R vials containing 1 ml of G-CSF formulation. Each sample was vortexed for 120 seconds.

2.3 Freeze/Thaw-Cycles

For freeze/thaw-cycles, samples were repeatedly frozen an thawed. 2R vials containing 1 ml of G-CSF formulation were evaluated for 5 and 10 cycles. All samples where held for 30 min before measurement to allow aggregation formation.

3. Aggregation Analysis 3.1 Analysis by Scattered Light (Turbidity) Measurement

For aggregation analysis by turbidity measurements, undiluted G-CSF formulations were tested by scattered light measurements in glass cuvettes on a HACH Nephelometer 2100AN with standard G-CSF solutions as a reference in a manner known per se. The scattered light that is diffusely deflected by the liquid is measured at an angle of 90° an comparison to standard suspensions. Values are given in Nephelometric Turbidity Units (NTU).

3.2 Non-Reducing SDS-PAGE (Sodium Dodecyl Sulphate Polyacrylamide Gel Electrophoresis)

Aggregation analysis by SDS-PAGE was performed on 4-12% BIS-TRIS Gels in non-reducing mode. Electrophoresis was carried out according to standard procedures as described, for example, in European Pharmacopoeia 5.0. Visualization was done by silver staining according to usual protocols. Bands with a molecular weight higher than that of monomeric G-CSF were counted.

3.3 Size Exclusion Chromatography (SEC)

Aggregation analysis by SEC was performed according to standard procedures (PHARMEUROPA, Vol. 19, No. 1 (2007) page 89, right column, "Impurities with molecular masses higher than that of filgrastim") using hydrophilic silica gel at 30° C. as a stationary phase. Elution was carried out using a phosphate buffered ammonium hydrogen carbonate solution as a mobile phase at a flow rate of 0.5 ml/min. Spectrophotometric detection was at 215 nm. The chromatograms were quantified, differentiating G-CSF monomers and higher aggregates. The results are expressed as percent peak area (% Peak area).

3.4 Reversed Phase (RP) HPLC

Analysis of the G-CSF content in samples after long term storage using RP-HPLC was performed according to standard procedures (see, PHARMEUROPA, Vol. 19, No. 1 (2007) page 91, "Related proteins."). Briefly, chromatography was carried out at a temperature of 65° C. using octadecylsilyl silica gel for chromatography having a pore size of 20 nm as a stationary phase and a column having a length of 0.15 m and a diameter of 4.6 mm. The mobile phase was a mixture consisting of 500 ml of water, 499 ml of acetonitril and 1 ml of trifluoroacetic acid. Flow rate was 1.0 ml/min and spectrophotometric detection was at 215 nm. Protein content was determined against a G-CSF reference standard.

Example 1

Effect of Buffer System on Temperature Stability

To study temperature stability and shelf life of the G-CSF formulations of the invention, the following formulations were prepared and compared with common buffers such as acetate, succinate and Tris. The formulations used in these experiments are shown in Table 1 below.

TABLE 1

G-CSF formulations with different buffer systems

| Components | Formulation 1 | 2 | 3 | 4 | 5 | 6 | 7 | 8 |
|---|---|---|---|---|---|---|---|---|
| G-CSF [mg/ml] | 0.6 | 0.6 | 0.6 | 0.6 | 0.6 | 0.6 | 0.6 | 0.6 |
| Sorbitol [mg/ml] | 50 | 50 | 50 | 50 | 50 | 50 | 50 | 50 |
| Poloxamer 188 [mg/ml] | 1 | 10 | 1 | 10 | 1 | 10 | 1 | 10 |
| Acetate [mM] | 10 | 10 | | | | | | |
| Succinate [mM] | | | 10 | 10 | | | | |
| Glutamate [mM] | | | | | 10 | 10 | | |
| Tris [mM] | | | | | | | 10 | 10 |
| pH | 4.0 | 4.0 | 4.0 | 4.0 | 4.0 | 4.0 | 7.2 | 7.2 |

The formulations (1 ml each) were stored for 7 days at 2-8° C., 25° C., 37° C. and <−15° C., and stability was determined by non-reducing SDS-PAGE as described above by counting the number of bands with a molecular weight higher than that of monomeric G-CSF compared to standard G-CSF preparations at T0 (Time 0). The number of bands seen in the gels in addition to monomeric G-CSF is shown in Table 2.

TABLE 2

Temperature Stability of G-CSF in different buffer systems

| Formulation | T0 | 7 days <−15° C. | 2-8° C. | 25° C. | 37° C. |
|---|---|---|---|---|---|
| 1 | — | — | — | — | — |
| 2 | — | — | — | — | — |
| 3 | 1 | 3 | 1 | 1 | 1 |
| 4 | — | — | — | — | — |

TABLE 2-continued

Temperature Stability of G-CSF in different buffer systems

| Formulation | T0 | 7 days | | | |
|---|---|---|---|---|---|
| | | <−15° C. | 2-8° C. | 25° C. | 37° C. |
| 5 | — | — | — | — | — |
| 6 | — | — | — | — | — |
| 7 | 1 | nd | nd | nd | nd |
| 8 | — | nd | nd | nd | nd | nd: not determined, because the solution was not clear at visual inspection indicating non-soluble aggregates
—: no bands in addition to monomeric G-CSF At visual inspection (data not shown), all vials containing acetate or glutamate and 0.1% or 1.0% Poloxamer 188 were clear solutions at all storage conditions. This correlates well with non-reducing SDS-PAGE where no bands other than monomeric G-CSF were detectable. Succinate formulations containing 0.1% Poloxamer 188 were clear at visual inspection or showed only small particles. Additional bands, however, were detectable at non-reducing SDS-PAGE, indicating soluble aggregates at all storage conditions even at T0. This effect is particularly pronounced after thawing from <−15° C. Stabilization was possible with higher concentrations of the surfactant, i.e., 10 mg/ml Poloxamer 188. All Tris-containing formulations showed fibrous particles or were turbid solutions on visual inspection; therefore, no SDS-PAGE was performed.

The results show that glutamate-buffered formulations allow good stabilization of G-CSF at various temperatures and after freezing and thawing. Stability is comparable to that of acetate-buffered formulations, even at low concentrations of the surfactant. In contrast, succinate-buffered formulations show quick formation of soluble and visible aggregates and can be stabilized only with higher concentrations of the surfactant. Tris-buffered formulations show soluble and visible aggregates at all Poloxamer concentrations tested.

Example 2

Stability of G-CSF Formulations Under Conditions of Mechanical Stress

To study the stability of the G-CSF formulations of the invention under conditions of mechanical stress, G-CSF formulations with buffer concentrations of 5 mM, 10 mM and 50 mM and pH values of 4.0, 4.4 and 5.0 were prepared. Comparison with acetate and citrate buffers was carried out at a buffer concentration of 10 mM of each buffer. The formulations used in these experiments are shown in Table 3 below.

TABLE 3

G-CSF formulations for testing under stress conditions

| Formulation | G-CSF (mg/ml) | Glutamate (mM) | Acetate (mM) | Citrate (mM) | pH | Sorbitol (mg/ml) | Tween 80 (mg/ml) |
|---|---|---|---|---|---|---|---|
| 9 | 0.96 | 5 | | | 4.0 | 50 | 0.04 |
| 10 | 0.96 | 5 | | | 4.4 | 50 | 0.04 |
| 11 | 0.96 | 5 | | | 5.0 | 50 | 0.04 |
| 12 | 0.96 | 10 | | | 4.0 | 50 | 0.04 |
| 13 | 0.96 | 10 | | | 4.4 | 50 | 0.04 |
| 14 | 0.96 | 10 | | | 5.0 | 50 | 0.04 |
| 15 | 0.96 | 50 | | | 4.0 | 50 | 0.04 |
| 16 | 0.96 | 50 | | | 4.4 | 50 | 0.04 |
| 17 | 0.96 | 50 | | | 5.0 | 50 | 0.04 |
| 18 | 0.96 | | 10 | | 4.0 | 50 | 0.04 |
| 19 | 0.96 | | 10 | | 4.4 | 50 | 0.04 |
| 20 | 0.96 | | 10 | | 5.0 | 50 | 0.04 |
| 21 | 0.96 | | | 10 | 4.0 | 50 | 0.04 |
| 22 | 0.96 | | | 10 | 4.4 | 50 | 0.04 |
| 23 | 0.96 | | | 10 | 5.0 | 50 | 0.04 |

The formulations were either untreated (T0) or subjected to shaking at 180 and 230 apm for 16 and 24 h, respectively, and vortexing for 120 s. Scattered light measurement and SEC were performed as described above under "Material and Methods" to test formation of aggregates. The results are shown in Table 4 and in FIG. 1.

TABLE 4

Physical Stability of G-CSF formulations under Conditions of Stress

| STRESS CONDITIONS | Buffer [mM] | pH | Glutamate | | | Acetate | | | Citrate | | |
|---|---|---|---|---|---|---|---|---|---|---|---|
| | | | SEC Purity [%] | | Clarity | SEC Purity [%] | | Clarity | SEC Purity [%] | | Clarity |
| | | | Agg. | G-CSF | NTU | Agg. | G-CSF | NTU | Agg. | G-CSF | NTU |
| T0 | 5 | 4.0 | 0.0 | 100.0 | 0.43 | | | | | | |
| | 5 | 4.4 | 0.0 | 100.0 | 0.27 | | | | | | |
| | 5 | 5.0 | 0.0 | 100.0 | 0.53 | | | | | | |
| | 10 | 4.0 | 0.0 | 100.0 | 0.34 | 0.1 | 99.9 | 0.26 | 0.0 | 100.0 | 0.40 |
| | 10 | 4.4 | 0.0 | 100.0 | 0.30 | 0.1 | 99.9 | 0.24 | 0.1 | 99.9 | 0.68 |
| | 10 | 5.0 | 0.0 | 100.0 | 0.54 | 0.1 | 99.9 | 0.47 | 0.1 | 99.9 | 0.70 |
| | 50 | 4.0 | 0.0 | 100.0 | 0.23 | | | | | | |
| | 50 | 4.4 | 0.0 | 100.0 | 0.22 | | | | | | |
| | 50 | 5.0 | 0.0 | 100.0 | 0.43 | | | | | | |
| Shaking 16 h at 180 apm | 5 | 4.0 | 1.6 | 98.4 | 0.44 | | | | | | |
| | 5 | 4.4 | 17.4 | 82.6 | 0.30 | | | | | | |
| | 5 | 5.0 | 81.0 | 19.0 | nd | | | | | | |
| | 10 | 4.0 | 0.9 | 99.1 | 0.27 | 0.6 | 99.4 | 0.21 | 70.2 | 29.8 | nd |
| | 10 | 4.4 | 10.0 | 90.0 | 0.29 | 26.7 | 73.3 | 0.58 | 27.6 | 72.4 | nd |

TABLE 4-continued

Physical Stability of G-CSF formulations under Conditions of Stress

| STRESS CONDITIONS | Buffer [mM] | pH | Glutamate SEC Purity [%] Agg. | Glutamate SEC Purity [%] G-CSF | Glutamate Clarity NTU | Acetate SEC Purity [%] Agg. | Acetate SEC Purity [%] G-CSF | Acetate Clarity NTU | Citrate SEC Purity [%] Agg. | Citrate SEC Purity [%] G-CSF | Citrate Clarity NTU |
|---|---|---|---|---|---|---|---|---|---|---|---|
|  | 10 | 5.0 | 84.3 | 15.7 | nd | 83.3 | 16.7 | nd | 28.8 | 71.2 | nd |
|  | 50 | 4.0 | 0.3 | 99.7 | 0.32 |  |  |  |  |  |  |
|  | 50 | 4.4 | 6.1 | 93.9 | 0.25 |  |  |  |  |  |  |
|  | 50 | 5.0 | 66.7 | 33.3 | nd |  |  |  |  |  |  |
| Shaking | 5 | 4.0 | 2.4 | 97.6 | 0.25 |  |  |  |  |  |  |
| 24 h at 230 apm | 5 | 4.4 | 44.0 | 56.0 | 0.34 |  |  |  |  |  |  |
|  | 5 | 5.0 | 93.7 | 6.3 | nd |  |  |  |  |  |  |
|  | 10 | 4.0 | 1.1 | 98.9 | 0.32 | 0.8 | 99.2 | 0.26 | 62.4 | 37.6 | nd |
|  | 10 | 4.4 | 32.6 | 67.4 | 0.25 | 58.1 | 41.9 | 0.47 | 26.5 | 73.5 | nd |
|  | 10 | 5.0 | 75.9 | 24.1 | nd | 77.3 | 22.7 | nd | 24.7 | 75.3 | nd |
|  | 50 | 4.0 | 0.4 | 99.6 | 0.31 |  |  |  |  |  |  |
|  | 50 | 4.4 | 8.2 | 91.8 | 0.40 |  |  |  |  |  |  |
|  | 50 | 5.0 | 31.2 | 68.8 | nd |  |  |  |  |  |  |
| Vortexing 120 sec | 5 | 4.0 | 0.3 | 99.7 | 0.20 |  |  |  |  |  |  |
|  | 5 | 4.4 | 2.7 | 97.3 | 0.36 |  |  |  |  |  |  |
|  | 5 | 5.0 | 4.3 | 95.7 | nd |  |  |  |  |  |  |
|  | 10 | 4.0 | 0.2 | 99.8 | 0.41 | 0.5 | 99.5 | 0.28 | 0.9 | 99.1 | nd |
|  | 10 | 4.4 | 1.7 | 98.3 | 1.0 | 3.7 | 96.3 | 0.35 | 2.5 | 97.5 | nd |
|  | 10 | 5.0 | 4.9 | 95.1 | 4.1 | 4.4 | 95.6 | 1.4 | 5.3 | 94.7 | nd |
|  | 50 | 4.0 | 0.1 | 99.9 | 0.4 |  |  |  |  |  |  |
|  | 50 | 4.4 | 2.1 | 97.9 | 0.3 |  |  |  |  |  |  |
|  | 50 | 5.0 | 4.0 | 96.0 | 17.5 |  |  |  |  |  |  |

Nd: not detectable
NTU: Nephelometric Turbidity Units
SEC Purity [%]: % peak area of monomeric G-CSF (G-CSF) and higher aggregates (Agg.) following SEC From the results shown in Table 4 and in FIG. 1, it may be seen that stability of glutamate-buffered G-CSF formulations under conditions of stress at all buffer concentrations is best at pH 4.0 and pH 4.4, but decreases rapidly at pH 5.0. Stability may also be increased by increasing the buffer concentration.

Shaking

At a buffer concentration of 10 mM, at a pH value of 4.0, glutamate and acetate buffered formulations show only minor decreases in G-CSF monomer levels following 16 h shaking at 180 apm (99.1% and 99.4%, respectively), while G-CSF monomer levels in citrate buffered formulations at pH 4.0 dropped drastically (29.8%). At a pH value of 4.4, at 16 h shaking G-CSF monomer levels are decreased to 90% for glutamate-buffered formulations. The decrease is considerably more pronounced, however, with acetate-buffered formulations (73.3%) and citrate-buffered formulations (72.4%). Having regard to glutamate- and acetate-buffered formulations, this phenomenon is also observed when samples are subjected to shaking for 24 h at 230 apm. Compared to citrate-buffered formulations, glutamate-buffered formulations are only slightly inferior. At pH values of 5.0, citrate buffered formulations have the highest content of G-CSF monomer.

Vortexing

Having regard to pH and buffer concentration, stability of G-CSF formulations at vortexing follows a similar pattern as observed in the shaking experiments discussed above. At 10 mM buffer concentration, stability of glutamate-buffered formulations is superior or at least equivalent to acetate- and citrate-buffered formulations at all pH values tested.

Example 3

Stability of Glutamate-Buffered G-CSF Formulations Under Conditions of Mechanical Stress in the Absence of Surfactant In order to test stress resistance of glutamate-buffered G-CSF formulations which are free from other components such as surfactants and tonicity agents, the following aqueous formulations were prepared (Table 5).

TABLE 5

G-CSF formulations without surfactants

| Formulation | G-CSF (mg/ml) | Glutamate (mM) | Acetate (mM) | pH |
|---|---|---|---|---|
| 24 | 0.96 |  | 10 | 4.4 |
| 25 | 0.96 | 10 |  | 4.4 |

Formulations were tested for stability under conditions of shaking and vortexing as described in Example 2, except that shaking was only continued for 16 h at 180 apm. The results are shown in Table 6. FIG. 2 shows represents SEC purity of these formulations.

TABLE 6

Physical Stability of G-CSF formulations in the absence of surfactant

| Formulation | 24 (Acetate) SEC Purity [%] Agg. | 24 (Acetate) SEC Purity [%] G-CSF | 24 (Acetate) Clarity NTU | 25 (Glutamate) SEC Purity [%] Agg. | 25 (Glutamate) SEC Purity [%] G-CSF | 25 (Glutamate) Clarity NTU |
|---|---|---|---|---|---|---|
| T0 | 0.3 | 99.7 | 0.52 | 0.3 | 99.7 | 0.366 |
| Vortexing 120 sec | 16.9 | 83.1 | 0.609 | 11.1 | 88.9 | 0.474 |

TABLE 6-continued

Physical Stability of G-CSF formulations in the absence of surfactant

| | 24 (Acetate) | | | 25 (Glutamate) | | |
|---|---|---|---|---|---|---|
| | SEC Purity [%] | | Clarity | SEC Purity [%] | | Clarity |
| Formulation | Agg. | G-CSF | NTU | Agg. | G-CSF | NTU |
| Shaking 16 h at 180 apm | 6.6 | 93.4 | 1.62 | 5.0 | 95 | 1.28 |

From the results in Table 6 it is seen that the glutamate-buffered formulations are more resistant to shaking and vortexing than acetate-buffered formulations. This confirms the above results and shows that this favourable effect is a consequence of the buffer and independent of the surfactant.

Example 4

Stability of G-CSF Formulations Following Repeated Freezing and Thawing

Formulations 13 and 19 shown in Table 4 were subjected to repeated freeze/thaw-cycles as described under "Materials and Methods". A 10 mM aqueous glutamate-buffer without G-CSF was used as a control. Samples were analyzed by SEC as described above. The results are shown in Table 7 below.

TABLE 7

Freeze/thaw-stability of G-CSF formulations

| Formulation | 13 (Glutamate) SEC Purity [%] | | 19 (Acetate) SEC Purity [%] | |
|---|---|---|---|---|
| Freeze/Thaw-Cycles | Agg. | G-CSF | Agg. | G-CSF |
| 5 cycles | <0.1 | 99.9 | <0.1 | 99.9 |
| 10 cycles | <0.1 | 99.9 | <0.1 | 99.9 |
| 10 cycles/Control | <0.1 | 99.9 | <0.1 | 99.9 |

As may be seen, glutamate-buffered formulations at pH 4.4 are stable upon repeated freezing and thawing, showing no loss of monomeric G-CSF. The results are comparable to acetate-buffered formulations.

Example 5

Long-Term Stability of G-CSF Formulations

Long-term stability of glutamate-buffered G-CSF formulations at different pH values was tested with the preparations listed in Table 8:

TABLE 8

G-CSF formulations for long-term storage

| | Formulation | | | | | |
|---|---|---|---|---|---|---|
| Components | 26 | 27 | 28 | 29 | 30 | 31 |
| G-CSF [mg/ml] | 0.6 | 0.6 | 0.6 | 0.96 | 0.96 | 0.96 |
| Sorbitol [mg/ml] | 50 | 50 | 50 | 50 | 50 | 50 |
| Tween 80 [mg/ml] | 0.04 | 0.04 | 0.04 | 0.04 | 0.04 | 0.04 |
| Glutamate [mM] | 10 | 10 | 10 | 10 | 10 | 10 |
| pH | 4.2 | 4.4 | 4.6 | 4.2 | 4.4 | 4.6 |

0.5 ml samples of the above preparations were stored in 1 ml syringes for 24 months (5° C.) or 6 months (25° C.) without shaking, and samples were taken at various time points and tested for monomeric G-CSF and aggregates by SEC as described above. The results for monomeric G-CSF are given in Table 9 below as % peak area.

At the same time, samples were taken to determine the protein content of G-CSF [µg/ml] by RP-HPLC as described above under "Materials and Methods", Section 3.4. The G-CSF content at the starting point, T0, was taken as 100%, and the G-CSF content at the respective measuring time was calculated based on the protein content at the starting point. The results are shown in Table 10 below.

TABLE 9

Stability of G-CSF in glutamate-buffered G-CSF formulations after long-term storage at 5° C. and 25° C.

| | | Formulation/G-CSF monomer in % Peak area | | | | | |
|---|---|---|---|---|---|---|---|
| Months | Days | 26 | 27 | 28 | 29 | 30 | 31 |
| Storage period at 5° C. | | | | | | | |
| 0 | 0 | 99.9 | 99.9 | 99.5 | 99.2 | 99.9 | 99.9 |
| 1 | 28 | 99.9 | | | 100.0 | | |
| 2 | 64 | 99.2 | | | 99.3 | | |
| 3 | 92 | 99.9 | | | 99.8 | | |
| 6 | 174 | 100.0 | 99.9 | 99.9 | 100.0 | 99.9 | 99.9 |
| 9 | 267 | 100.0 | 99.9 | 99.8 | 100.0 | 99.9 | 99.5 |
| 12 | 327 | 99.9 | 99.9 | 99.9 | 100.0 | 99.9 | 99.8 |
| 18 | 541 | 99.9 | 99.6 | 99.8 | 99.8 | 99.8 | 99.6 |
| 24 | 733 | 99.9 | 99.9 | 99.8 | 99.8 | 99.8 | 99.1 |
| Storage period at 25° C. | | | | | | | |
| 0 | 0 | 99.9 | 99.9 | 99.5 | 99.2 | 99.9 | 99.9 |
| 1 | 28 | 99.9 | | | 98.8 | | |
| 2 | 64 | 99.1 | | | 98.7 | | |
| 3 | 92 | 99.4 | | | 99.4 | | |
| 6 | 174 | 99.1 | 98.5 | 98.3 | 99.4 | 98.7 | 97.8 |

The results in Table 9 show that loss of monomeric G-CSF over time is very low at any tested pH value, and that glutamate-buffered G-CSF formulations are sufficiently stable for at least 24 months at 5° C. and for at least 6 months at 25° C.

TABLE 10

Stability of G-CSF in glutamate-buffered G-CSF formulations after long-term storage at 5 and 25° C.

| Storage period At 5° C. | | Formulation/ G-CSF content in % of initial content | | | | | |
|---|---|---|---|---|---|---|---|
| Months | Days | 26 | 27 | 28 | 29 | 30 | 31 |
| 0 | 0 | 100 | 100 | 100 | 100 | 100 | 100 |
| 6 | 174 | 98.1 | 97.8 | 98.0 | 95.8 | 95.7 | 97.2 |
| 9 | 267 | 97.9 | 96.9 | 97.8 | 97.6 | 98.4 | 99.1 |
| 12 | 327 | 96.2 | 95.4 | 95.5 | 97.1 | 96.7 | 97.6 |
| 18 | 541 | 98.1 | 98.1 | 97.8 | 98.4 | 97.8 | 99.0 |
| 24 | 733 | 96.2 | 96.4 | 95.3 | 95.8 | 95.7 | 96.1 |
| Storage period at 25° C. | | Formulation/ G-CSF content in % of starting value | | | | | |
| Months | Days | 26 | 27 | 28 | 29 | 30 | 31 |
| 0 | 0 | 100 | 100 | 100 | 100 | 100 | 100 |
| 1 | 28 | 94.9 | | | 95.2 | | |
| 2 | 64 | 94.2 | | | 94.5 | | |

TABLE 10-continued

Stability of G-CSF in glutamate-buffered G-CSF
formulations after long-term storage at 5 and 25° C.

| 3 | 92  | 92.3 |      |      | 92.4 |      |      |
|---|-----|------|------|------|------|------|------|
| 6 | 174 | 90.8 | 91.4 | 92.2 | 92.2 | 92.9 | 92.1 |

The results in Table 10 show that there is only a minor loss of G-CSF protein at long term storage at any tested pH value. Over all samples tested the G-CSF content is at least 95% of the initial G-CSF content after 24 months of storage at a temperature of 5° C. and at least 90% after 6 months of storage at a temperature of 25° C.

The invention claimed is:

1. A stable liquid aqueous glutamic acid/glutamate-buffered Granulocyte-Colony Stimulating Factor (G-CSF) formulation having a pH of from 3.5 to 4.8, said formulation comprising a non-ionic surfactant and being essentially free from amino acids/amino acid salts other than glutamic acid/glutamate.

2. The formulation of claim 1, wherein the pH of the formulation is of from 4.2 to 4.6.

3. The formulation of claim 1, wherein the glutamate, in the form of glutamic acid and/or a salt thereof, is present in a concentration of from 2 to 100 mM.

4. The formulation of claim 1, wherein G-CSF is present in a concentration of from 0.1 to 1.5 mg/ml.

5. The formulation of claim 1, wherein the non-ionic surfactant is selected from the group consisting of fatty alcohol ethoxylates, alkylpolyglycosides, polyoxyalkylenes, polysorbates or mixtures of two or more thereof.

6. The formulation of claim 5, wherein the surfactant is a polysorbate or a mixture of polysorbates, preferably selected from the group consisting of polyoxyethylene sorbitan monolaurate, polyoxyethylene sorbitan monooleate, polyoxyethylene sorbitan monostearate, polyoxyethylene-sorbitan mono palmitate, polyoxyethylene sorbitan trioleate and polyoxyethylene sorbitan tristearate.

7. The formulation of claim 1, further comprising a tonicity agent.

8. The formulation of claim 7, wherein the tonicity agent is sorbitol.

9. The formulation of claim 1, wherein the formulation is essentially free from sugars and aminosugars.

10. The formulation of claim 1, wherein the G-CSF content of the formulation after long term storage at 5° C. for 24 months is at least 95% of the initial G-CSF content, as determined by RP-HPLC.

11. The formulation of claim 1, wherein the G-CSF content of the formulation after long term storage at 25° C. for 6 months is at least 90% of the initial G-CSF content, as determined by RP-HPLC.

12. The formulation of claim 1 which is a pharmaceutically acceptable formulation.

13. The formulation of claim 12, wherein the pharmaceutical formulation is a solution for injection or infusion.

14. A lyophilisate or a powder comprising G-CSF obtainable by lyophilization or spray-drying, respectively, from an aqueous formulation as defined in claim 1.

15. The pharmaceutical kit for preparing an aqueous formulation as defined in claim 12, comprising, physically separated:
   a) a G-CSF-containing lyophilisate or powder; and
   b) a glutamate-buffered aqueous solution having a pH value of from 3.5 to 4.8 for reconstituting the G-CSF-containing lyophilisate or powder.

16. A method for preparing a formulation as defined in claim 1, comprising combining G-CSF with a glutamate-buffered aqueous solution having a pH value of from 3.5 to 4.8.

17. A method for preparing a lyophilisate or a powder as defined in claim 14, comprising lyophilizing or spray-drying a formulation as defined in claim 1.

18. A hydrogel or liposome preparation, comprising a formulation as defined in claim 1.

* * * * *